(12) United States Patent
Tanaka et al.

(10) Patent No.: US 10,435,383 B2
(45) Date of Patent: Oct. 8, 2019

(54) C-GLYCOSIDE DERIVATIVES

(71) Applicant: OKINAWA INSTITUTE OF SCIENCE AND TECHNOLOGY SCHOOL CORPORATION, Okinawa (JP)

(72) Inventors: Fujie Tanaka, Okinawa (JP); Sherida Johnson, Okinawa (JP)

(73) Assignee: OKINAWA INSTITUTE OF SCIENCE AND TECHNOLOGY SCHOOL CORPORATION, Okinawa (JP)

( * ) Notice: Subject to any disclaimer, the term of this patent is extended or adjusted under 35 U.S.C. 154(b) by 0 days.

(21) Appl. No.: 15/560,858

(22) PCT Filed: Feb. 1, 2016

(86) PCT No.: PCT/JP2016/000506
§ 371 (c)(1),
(2) Date: Sep. 22, 2017

(87) PCT Pub. No.: WO2016/151989
PCT Pub. Date: Sep. 29, 2016

(65) Prior Publication Data
US 2018/0118703 A1    May 3, 2018

Related U.S. Application Data

(60) Provisional application No. 62/137,380, filed on Mar. 24, 2015.

(30) Foreign Application Priority Data

Jul. 31, 2015  (JP) .................................. 2015-152437

(51) Int. Cl.
*C07D 307/22*    (2006.01)
*C07D 309/14*    (2006.01)

(52) U.S. Cl.
CPC ......... *C07D 307/22* (2013.01); *C07D 309/14* (2013.01)

(58) Field of Classification Search
CPC ............................ C07D 307/22; C07D 309/14
See application file for complete search history.

(56) References Cited

U.S. PATENT DOCUMENTS

| 8,314,219 B1 | 11/2012 | Price |
| 2003/0176363 A1 | 9/2003 | Cowden et al. |
| 2009/0274638 A1 | 11/2009 | Pineau et al. |
| 2011/0245490 A1 | 10/2011 | Benvegnu et al. |

FOREIGN PATENT DOCUMENTS

| WO | 02/04472 | 1/2002 |
| WO | 02/051803 | 7/2002 |
| WO | 2008/003900 | 1/2008 |

OTHER PUBLICATIONS

Voigt et al., Chem. Commun., 2014, 50, p. 817-819. (Year: 2014).*
International Search Report dated Mar. 22, 2016 in International (PCT) Application No. PCT/JP2016/000506.
Bragnier et al., "One-step synthesis of β-C-glycosidic ketones in aqueous media: The case of 2-acetamido sugars", Synthesis, No. 5, 2005, pp. 814-818.
Dmitriev et al, "Monosaccharides. XIII. Synthesis of derivatives of 4-amino-4-deoxy sugars", Izvestiya Akademii Nauk SSSR, Seriya Khimicheskaya, No. 11, 1967, pp. 2483-2490, cited in ISR.
Organocatalytic tandem aldol condensation—Michael reactions of C6 pyranoses to synthesize C-glycosides [online] [retrieved on Feb. 23, 2016], Feb. 2, 2015, Retrieved from the Internet: <URL: http://nenkai.pharm.or.jp/135/web/ and http://nenkai.pharm.or.jp/135/pc/imulti_result.asp and http://nenkai.pharm.or.jp/135/pc/ipdfview.asp?i=3290>.
Johnson et al, "Direct synthesis of C-glycosides from unprotected 2-N-acyl-aldohexoses via aldol condensation-oxa-Michael reactions with unactivated ketones", Organic & Biomolecular Chemistry, vol. 14, No. 1, Nov. 2, 2015, pp. 259-264.
Scherrmann et al., "Knoevenagel Reaction of Unprotected Sugars", Top Curr. Chem., vol. 295, Mar. 23, 2010, pp. 1-18.
Lalitha et al., "Recent developments in β-C-glycosides: synthesis and applications", Carbohydrate Research, vol. 402, Oct. 24, 2014, pp. 158-171.
Buchieri et al., "Inhibition of the β-carbonic anhydrases from *Mycobacterium tuberculosis* with C-cinnamoyl glycosides: Identification of the first inhibitor with anti-mycobacterial activity", Bioorganic & Medicinal Chemistry Letters, vol. 23, Dec. 1, 2012, pp. 740-743.
Written Opinion dated Mar. 22, 2016 in International (PCT) Application No. PCT/JP2016/000506.

* cited by examiner

*Primary Examiner* — Jonathan S Lau
(74) *Attorney, Agent, or Firm* — Wenderoth, Lind & Ponack, L.L.P.

(57) ABSTRACT

The present invention can provide novel C-glycoside derivatives which are biologically important under high stereoselective, mild, atom economical condition.

9 Claims, No Drawings

C-GLYCOSIDE DERIVATIVES

TECHNICAL FIELD

The present invention relates to C-glycoside derivatives, methods for the preparation thereof. The present invention provides pharmaceutical composition comprising the C-glycoside derivatives and their use as therapeutically active substance thereof.

BACKGROUND ART

Preparation of C-glycosides has been reported which is prepared by Knoevenagel Condensation of sugars and 1,3-diketones, followed by elimination of acyl group (NPL 1).

C-glycoside is a building block which is found in biologically important compounds. C-glycoside is more stable than O-, N-, S-glycosides due to resistance against acid, enzyme, and hydrolysis (NPL 2). Further, C-glycoside derivatives has been biological active substances (NPL 3).

CITATION LIST

Non Patent Literature

NPL 1: M.-C. Scherrmann, Top. Curr. Chem. 2010, 295, 1-18.
NPL 2: K. Lalitha, K. Muthusamy, Y. S. Prasad, P. K. Vemula, S. Nagarajan, Carbohydr. Res. 2015, 402, 158-171.
NPL 3: M. V. Buchieri, etc., Bioorg. Med. Chem. Lett. 2013, 23, 740-743.

SUMMARY OF INVENTION

Technical Problem

The technical problem to be solved by the present invention is that of providing novel C-glycoside derivatives which are biologically important. The technical problem to be solved by the present invention is also that of providing methods for preparation of the novel C-glycoside derivatives under high stereoselective, mild, atom economical condition.

Solution to Problem

The present invention can provide novel C-glycoside derivatives by aldol condensation of unprotected sugars and ketones such as acetone, followed by oxa-Michael annulation under high stereoselective, mild, atom economical condition.

The present invention relates as follows.

(1) A process for the manufacture of compounds of formula I or II:

[Chem.1]

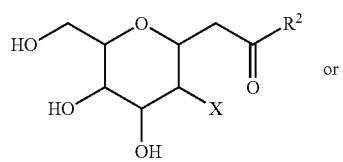

I or

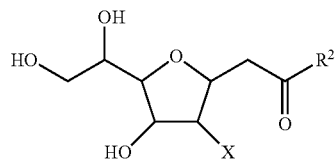

II wherein
X is OH or $NHCOR^1$,
$R^1$ is $C_{1-7}$alkyl, $C_{3-7}$cycloalkyl, halo-$C_{1-7}$alkyl, or $C_{1-7}$alkoxy-$C_{1-7}$alkyl, and
$R^2$ is $C_{1-7}$alkyl, $C_{3-7}$cycloalkyl, halo-$C_{1-7}$alkyl, $C_{1-7}$alkoxy, halo-$C_{1-7}$alkoxy, or $C_{1-7}$ alokoxy-$C_{1-7}$alkyl, comprising step A):
reacting compound of formula III:

[Chem.2]

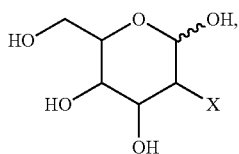

III wherein X is as defined above, with compound of formula IV:

[Chem.3]

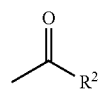

IV wherein $R^2$ is as defined above, in the presence of primary or secondary amine, and additive.

(2) The process according to (1), wherein primary or secondary amine, and additive is selected from the group consisting of
(a) pyrrolidine and $H_3BO_3$,
(b) pyrrolidine and $H_3BO_3$,
(c) L-proline and $iPr_2NEt$,
(d) L-proline, $iPr_2NEt$, and cis-4-hydroxy-cyclohexane carboxylic acid, and
(e) D-proline and $iPr_2NEt$ (3) The process according to (1), further comprising a step B):
compound I or II:

[Chem. 4]

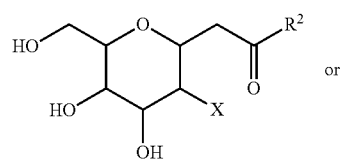

I or

-continued

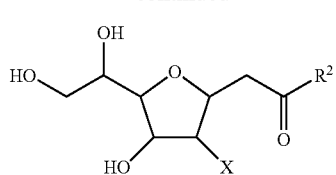

II wherein X, R¹, and R² are as defined above, with reactant to obtain compound of formula I-1, II-1, I-2, or II-2:

[Chem.5]

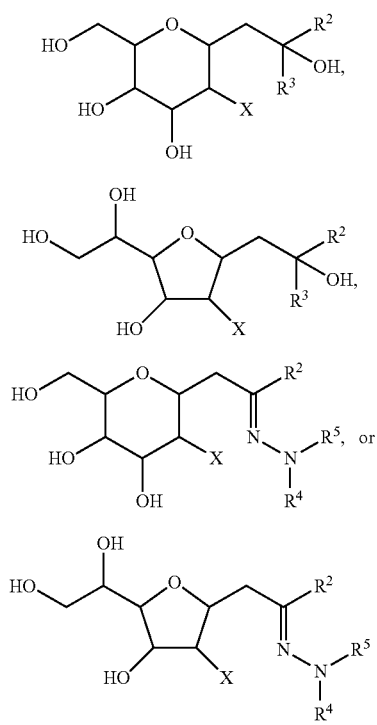

wherein
X, R¹, and R² are as defined in (1),
R³ is $C_{1-7}$alkyl, $C_{2-7}$alkenyl, and $C_{2-7}$alkyynyl, and
R⁴ and R⁵ may be same or different, and each is independently selected from the group consisting of H, $C_{1-7}$alkyl, phenyl, benzyl, piperidinyl, p-tosyl and 1-phtalazinyl.

(4) The process according to (3), wherein reactant is allyl bromide and indium, or p-toluenesulfonyl hydrazide.

(5) The compound of formula I, II, I-1, II-1, I-2, or II-2, which is manufactured according to a process of any one of (1) to (4).

(6) The compound of formula I-1, II-1, I-2, or II-2 according to (3), or salts thereof.

(7) The compound of formula I, II, I-1, II-1, I-2, or II-2, selected from the group of
Compound 2a:
N-((2R,3S,4R,5S)-5-((R)-1,2-dihydroxyethyl)-4-hydroxy-2-(2-oxopropyl)tetrahydrofuran-3-yl)acetamide,
Compound 2b:
N-((2S,3S,4R,5S,6R)-4,5-dihydroxy-6-(hydroxymethyl)-2-(2-oxopropyl)tetrahydro-2H-pyran-3-yl)acetamide,
Compound 6a-1:
N-((2R,3R,4R,5S)-5-((R)-1,2-dihydroxyethyl)-4-hydroxy-2-(2-oxopropyl)tetrahydrofuran-3-yl)acetamide,
Compound 6a-2:
N-((2S,3R,4R,5S)-5-((R)-1,2-dihydroxyethyl)-4-hydroxy-2-(2-oxopropyl)tetrahydrofuran-3-yl)acetamide,
Compound 6b:
N-((2S,3R,4R,5S,6R)-4,5-dihydroxy-6-(hydroxymethyl)-2-(2-oxopropyl)tetrahydro-2H-pyran-3-yl)acetamide,
Compound 8a:
N-((2S,3R,4R,5S)-5-((R)-1,2-dihydroxyethyl)-4-hydroxy-2-(2-oxopropyl)tetrahydrofuran-3-yl)pentanamide,
Compound 8b:
N-((2S,3R,4R,5S,6R)-4,5-dihydroxy-6-(hydroxymethyl)-2-(2-oxopropyl)tetrahydro-2H-pyran-3-yl)pentanamide,
Compound 10a-1:
N-((2R,3R,4R,5R)-5-((R)-1,2-dihydroxyethyl)-4-hydroxy-2-(2-oxopropyl)tetrahydrofuran-3-yl)acetamide,
Compound 10a-2:
N-((2S,3R,4R,5R)-5-((R)-1,2-dihydroxyethyl)-4-hydroxy-2-(2-oxopropyl)tetrahydrofuran-3-yl)acetamide,
Compound 10b:
N-((2S,3R,4R,5R,6R)-4,5-dihydroxy-6-(hydroxymethyl)-2-(2-oxopropyl)tetrahydro-2H-pyran-3-yl)acetamide,
Compound 11:
N-((3R,4R,5S,6R)-4,5-dihydroxy-6-(hydroxymethyl)-2-(3-methoxy-2-oxopropyl)tetrahydro-2H-pyran-3-yl)acetamide,
Compound 12:
N-((2R,3S,4R,5S)-5-((R)-1,2-dihydroxyethyl)-4-hydroxy-2-(2-hydroxy-2-methylpent-4-en-1-yl)tetrahydrofuran-3-yl)acetamide,
Compound 13:
N-((2R,3S,4R,5S)-5-((R)-1,2-dihydroxyethyl)-4-hydroxy-2-(3-methoxy-2-oxopropyl)tetrahydrofuran-3-yl)acetamide, and
Compound 14:
N-((2R,3S,4R,5S)-5-((R)-1,2-dihydroxyethyl)-4-hydroxy-2-(2-(2-tosylhydrazono)propyl)tetrahydrofuran-3-yl)acetamide.

(8) A pharmaceutical composition comprising the compound of formula I, II, I-1, or II-1 according to any one of (5) to (7) or pharmaceutically acceptable salts thereof, and pharmaceutically acceptable adjuvant.

Advantageous Effects of Invention

The present invention can provide novel C-glycoside derivatives which are biologically important under high stereoselective, mild, atom economical condition.

DESCRIPTION OF EMBODIMENTS

In the present disclosure, certain details are set forth such as specific quantities, concentrations, sizes, etc. so as to provide a thorough understanding of the various embodiments disclosed herein. However, it will be apparent to those skilled in the art that the present disclosure may be practiced without such specific details. In many cases, details concerning such considerations and the like have been omitted inasmuch as such details are not necessary to obtain a complete understanding of the present disclosure and are within the skill of persons of ordinary skill in the relevant art.

The term "$C_{1-7}$alkyl", alone or in combination with other groups, denotes a monovalent linear or branched saturated hydrocarbon group of 1 to 7 carbon atoms, preferably 1 to 4 carbon atoms. Examples of $C_{1-7}$alkyl include methyl, ethyl, n-propyl, isopropyl, n-butyl, iso-butyl, sec-butyl, tert-butyl, pentyl, hexyl, and heptyl, preferably methyl, ethyl, n-propyl, isopropyl, n-butyl, iso-butyl, sec-butyl, tert-butyl, n-pentyl, and isopentyl, more preferably methyl, ethyl, propyl, isopropyl, isobutyl, tert-butyl, and isopentyl.

The term "$C_{2-7}$alkenyl", alone or in combination with other groups, denotes a monovalent linear or branched alkyl containing a double bond and comprising 2 to 7 carbon atoms, more preferably linear $C_{2-4}$alkenyl. Examples of alkenyl include vinyl, allyl, propenyl, and butenyl, etc., preferably allyl.

The term "$C_{2-7}$alkyynyl", alone or in combination with other groups, denotes a monovalent linear or branched alkyl containing a triple bond and comprising 2 to 7 carbon atoms, more preferably linear $C_{2-4}$alkynyl. Examples of alkynyl include ethynyl, and propargyl, etc., preferably ethynyl.

The term "$C_{3-7}$cycloalkyl", alone or in combination with other groups, denotes a monovalent saturated hydrocarbon group of 3 to 7 ring carbon atoms, preferably 3 to 6 ring carbon atoms. Examples of $C_{3-7}$cycloalkyl are cyclopropyl, cyclobutyl, cyclopentyl, and cyclohexyl.

The term "$C_{1-7}$alkoxy", alone or in combination with other groups, denotes a group of the formula $C_{1-7}$alkyl-O— wherein the term "$C_{1-7}$alkyl" is as defined above. Examples of $C_{1-7}$alkoxy include methoxy, ethoxy, n-propoxy, isopropoxy, n-butoxy, isobutoxy, sec-butoxy, and tert-butoxy.

The term "halo", alone or in combination with other groups, denotes halogen, for examples fluoro, chloro, bromo, or iodo, preferably fluoro, chloro, or bromo, more preferably fluoro and chloro. The term "halogen", in combination with other groups, denotes a substituent substituted with at least one halogen, preferably, 1 to 5 halogens, more preferably 1 to 4 halogens.

The term "halo-$C_{1-7}$alkyl", alone or in combination with other groups, denotes an $C_{1-7}$ alkyl group wherein at least one of the hydrogen atoms of the alkyl group has been replaced by same or different halogen atoms, preferably 1 to 5 halogen atoms, more preferably 1 to 3 halogen atoms. Examples of haloalkyl include fluoromethyl, difluoromethyl, trifluoromethyl, 1,1,1-trifluoroethyl, 1,1,1-trifluoropropyl and pentafluoroethyl.

The term "halo-$C_{1-7}$alkoxy", alone or in combination with other groups, denotes an $C_{1-7}$ alkoxy group wherein at least one of the hydrogen atoms of the alkoxy group has been replaced by same or different halogen atoms, preferably 1 to 5 halogen atoms, more preferably 1 to 3 halogen atoms. Examples of haloalkoxy include fluoromethoxy, difluoromethoxy, trifluoromethoxy, 1,1,1-trifluoroethoxy, 1,1,1-trifluoropropoxy, and pentafluoroethoxy.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like.

The compounds of formula I, II, I-1, II-1, I-2, or II-2 may contain several asymmetric centers and may be present in the form of optically pure enantiomers, mixtures of enantiomers, for example, racemates, optically pure diastereoisomers, mixtures of diastereoisomers, diastereoisomeric racemates or mixtures of diastereoisomeric racemates. Optically pure form may be obtained by e.g. optical resolution of racemates, asymmetric synthesis, or asymmetric chromatography (chromatography by use of chiral carrier or elutant)

According to the Cahn-Ingold-Prelog Convention the asymmetric carbon atom of the compound of formula I can be of the "R" or "S" configuration.

Abbreviation

DMSO: dimethyl sulfoxide
DMF: dimethyl formamide
$H_3BO_3$: boric acid
MeOH: methanol
iPr$_2$NEt: diisopropylmethylamine
THF: tetrahydrofuran Another aspects of the invention further include the methods for the preparation of compounds of formula I and II.

<Step A)>

In particular embodiments of the present invention, a process for the manufacture of compounds of formula I or II:

[Chem.6]

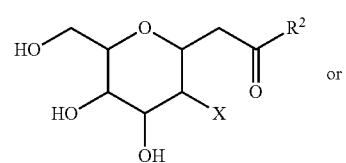

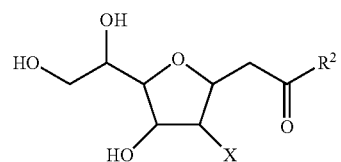

wherein
X is OH or NHCOR$^1$,
R$^1$ is $C_{1-7}$alkyl, $C_{3-7}$cycloalkyl, halo-$C_{1-7}$alkyl, or $C_{1-7}$alkoxy-$C_{1-7}$alkyl, and
R$^2$ is $C_{1-7}$alkyl, $C_{3-7}$cycloalkyl, halo-$C_{1-7}$alkyl, $C_{1-7}$alkoxy, halo-$C_{1-7}$alkoxy, or $C_{1-7}$ alokoxy-$C_{1-7}$alkyl,
includes step A):
reacting compound of formula III:

[Chem.7]

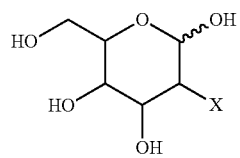

wherein X is as defined above, with compound of formula IV:

[Chem.8]

IV wherein $R^2$ is as defined above, in the presence of primary or secondary amine, and additive.

<General Method of Step A)>

Step A) includes reaction of the compound of III and compound of IV in the presence of primary or secondary amine, and additive to obtain compounds of formula I or II.

In particular embodiments of the invention, in step A), the molar ratio of compound of formula IV to compound of formula III is, for example, 2 to 100, preferably 5 to 40, more preferably 10 to 30.

In particular embodiments of the invention, in step A), primary or secondary amines can be used, for example, aliphatic amines (methylamine, dimethylamine, ethylamine, diethylamine, and the like), aromatic amines (aniline, pyrrole, imidazole, and the like), heterocyclic amines (pyrrolidine, piperidine, piperazine, morpholine, and the like), preferably a 5- or 6-membered heterocyclic secondary amines, more preferably, pyrrolidine, L-proline is D-proline.

In particular embodiments of the invention, in step A), at least one additive can be used, which is selected from the group, for example, tertiary amine, boronic compound, and hydroxycarboxylic acid derivative.

In particular embodiments of the invention, in step A), tertiary amine can be uses as an additive, for example, aliphatic amines (trimethylamine, triethylamine, diisopropylethylamine, and the like), an aromatic amine (pyridine, pyrimidine, and the like), preferably an aliphatic amine, more preferably diisopropylethylamine.

In particular embodiments of the invention, in step A), boronic compound can used as an additive, for example, boric acid ($H_3BO_3$), boronic acid (methyl boronic acid, phenyl boronic acid, and the like), a borinic acid (dimethyl borinic acids, diethyl borinic acid, and the like), preferably boric acid, phenyl boronic acid, and more preferably boric acid.

In particular embodiments of the invention, in step A), hydroxycarboxylic acid derivative can be used as an additive, for example, 5- or 6-membered hydroxycarboxylic acid derivative or amino acid derivative, preferably a cis-4-hydroxy-cyclohexanecarboxylic acid.

In particular embodiments of the invention, in step A), primary or secondary amine, and additive can be selected from the group of
(a) pyrrolidine and $H_3BO_3$,
(b) pyrrolidine and $H_3BO_3$,
(c) L-proline and $iPr_2NEt$,
(d) L-proline, $iPr_2NEt$, and cis-4-hydroxy-cyclohexane carboxylic acid, and
(e) D-proline and $iPr_2NEt$ In particular embodiments of the invention, in step A), the molar ratio of primary or secondary amines to compound of formula III is, for example, 0.05 to 1.0, preferably 0.1 to 0.8, more preferably 0.4 to 0.6.

In particular embodiments of the invention, in step A), the molar ratio of additives to compound of formula III is, for example, 0.05 to 5.0, preferably 0.2 to 3.0, more preferably 1.0 to 2.0.

In particular embodiments of the invention, in step A), the reaction can be carried out in a solvent, which is not limited unless the solvent is involved in the reaction, in a polar solvent such as MeOH, DMSO, and the like.

In particular embodiments of the invention, in step A), the reaction time, which is no limited if compound of formula III is consumed, for example, 12 to 120 hours, preferably 12 to 72 hours, more preferably 24 to 48 hours.

In particular embodiments of the invention, in step A), the reaction can be carried out, for example, at 10 to 60° C., preferably 15 to 40° C., more preferably 20 to 30° C.

<Step B)>

In particular embodiments of the present invention, a step B):

compound I or II:

[Chem.9]

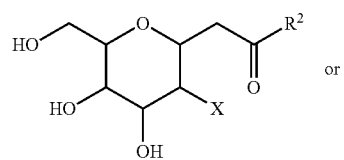

I

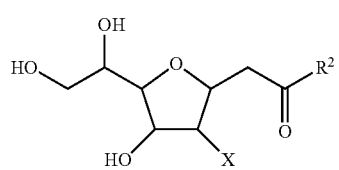

II wherein X, $R^1$, and $R^2$ are as defined above, with reactant to obtain compound of formula I-1, II-1, I-2, or II-2:

[Chem.10]

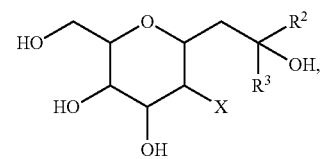

I-1

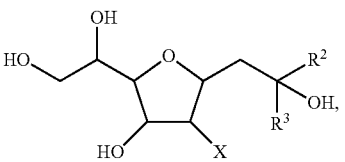

II-1

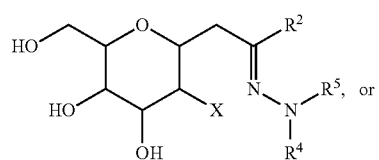

I-2

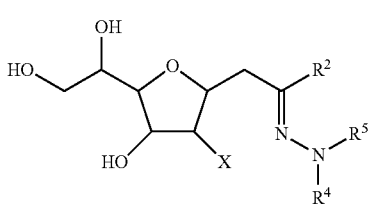

II-2 wherein

X, R$^1$, and R$^2$ are as defined in (1), and

R$^3$ is C$_{1-7}$alkyl, C$_{2-7}$alkenyl, and C$_{2-7}$alkyynyl, and

R$^4$ and R$^5$ may be same or different, and each is independently selected from the group consisting of H, C$_{1-7}$alkyl, phenyl, benzyl, piperidinyl, p-tosyl and 1-phtalazinyl.

<General Method of Step B)>

Step B) includes reaction of the compound of formula I or II with reactant to obtain compound of I-1, II-1, I-2, or II-2.

In particular embodiments of the invention, in step B), reactants can be used, for example, allyl bromide and indium; hydrazine derivatives; reactants used for aldol or aldol condensation and the like, preferably, allyl bromide and indium, or hydrazine derivatives. The hydrazine derivative includes, for example methyl hydrazine, dimethyl hydrazine, phenyl hydrazine, benzyl hydrazine, piperidine hydrazine, p-tosyl hydrazine, and 1-phtalazinyl hydrazine and the like, preferably p-tosyl hydrazine.

In particular embodiments of the invention, in step B), the amount of reactants to compound of formula I or II is no limited if compound of formula I or II is consumed.

In particular embodiments of the invention, in step B), the reaction can be carried out in a solvent, which is not limited unless the solvent is involved in the reaction, such as DMF, DMSO, MeOH, THF, and the like.

In particular embodiments of the invention, in step B), the reaction time, which is no limited if compound of formula I or II is consumed, for example, 10 to 24 hours.

In particular embodiments of the invention, in step B), the reaction can be carried out, for example, at 0 to 40° C.

The invention further relates to the compound of formula I, II, I-1, II-1, I-2, or II-2 for use as a therapeutically active substance.

Pharmaceutical Compositions

The invention further relates to pharmaceutical composition comprising the compound of formula I, II, I-1, II-1, I-2, or II-2 or pharmaceutically acceptable salts thereof, and pharmaceutically acceptable adjuvant.

The compounds of formula I, II, I-1, II-1, I-2, or II-2 as well as their pharmaceutically acceptable salts can be used as medicaments, e.g. in the form of pharmaceutical preparations. The pharmaceutical preparations can be administered orally, e.g. in the form of tablets, coated tablets, dragees, hard and soft capsules, solutions, emulsions or suspensions. The administration can however, also be effected rectally, e.g. in the form of suppositories, or parenterally, e.g. in the form of injection solutions.

The compounds of formula I, II, I-1, II-1, I-2, or II-2 and their pharmaceutically acceptable salts can be processed with pharmaceutically inert, inorganic or organic excipients for the production of tablets, coated tablets, dragees and hard gelatin capsules. Lactose, corn starch or derivatives thereof, talc, stearic acid or its salts etc. can be used as such excipients e.g. for tablets, dragees and hard gelatin capsules.

Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can be varied within wide limits and will, of course, be adapted to the individual requirements in each particular case. In general, in the case of oral administration a daily dosage of about 10 to 1000 mg per person of a compound of formula I, II, I-1, or II-1 should be appropriate, although the above upper limit may be exceeded when necessary.

EXAMPLES

The invention is illustrated hereinafter by Examples, which have no limiting character. In case the preparative examples are obtained as a mixture of enantiomers and diastereomers, the pure enantiomers or diastereomers may be separated by methods described herein or by methods known to the person skilled in the art, such as chiral chromatography and crystallization.

Example 1: Reaction Using L-Proline and N,N-Diisopropylethylamine as Catalyst

To a mixture of L-proline (24.0 mg, 0.209 mmol) in DMSO (1.0 mL), acetone (615 µL, 8.36 mmol) and N,N-diisopropylethylamine (36.0 µL, 0.209 mmol) were added at room temperature (25° C.), and the mixture was stirred for 5 min. To this mixture, N-acetyl-D-mannosamine monohydrate (100.0 mg, 0.418 mmol) was added and the resulting mixture was stirred at the same temperature for 96 h. The mixture was purified by silica gel flash column chromatography (CH$_2$Cl$_2$/MeOH=92:8 to 84:16 over 10 min and 84:16 for 25 min) to give 2a (72.8 mg, 62%).

Example 2: Reaction Using L-Proline and N,N-Diisopropylethylamine as Catalyst

To a mixture of L-proline (48.0 mg, 0.418 mmol) in DMSO (1.0 mL), acetone (1.23 mL, 16.7 mmol) and N,N-diisopropylethylamine (73.0 µL, 0.418 mmol) were added at room temperature (25° C.), and the mixture was stirred for 5 min. To this mixture, N-acetyl-D-mannosamine monohydrate (200.0 mg, 0.836 mmol) was added and the resulting mixture was stirred at the same temperature for 96 h. The mixture was purified by silica gel flash column chromatography (CH$_2$Cl$_2$/MeOH=92:8 to 84:16 over 10 min and 84:16 for 25 min) to give 2a (131.0 mg, 60%). Compound 2a was crystallized from acetone.

Example 3: Reaction Using L-Proline, N,N-Diisopropylethylamine, and cis-4-hydroxycyclohexanecarboxylic Acid as Catalyst A mixture of L-proline (24.0 mg, 0.209 mmol), DMSO (1.0 mL), acetone (615 µL, 8.36 mmol), N,N-diisopropylethylamine (81.0 µL, 0.627 mmol), cis-4-hydroxycyclohexanecarboxylic acid (60.0 mg, 0.418 mmol), and N-acetyl-D-mannosamine monohydrate (100.0 mg, 0.418 mmol) were stirred at room temperature (25° C.) for 48 h. The mixture was purified by silica gel flash column chromatography (CH$_2$Cl$_2$/MeOH=90:10 to 83:17 over 10 min and 83:17 for 25 min) to give 2a (51.0 mg, 44%).

Example 4: Reaction Using Pyrrolidine and Boric Acid as Catalyst

A mixture of pyrrolidine (17.0 µL, 0.209 mmol), H$_3$BO$_3$ (26.0 mg, 0.416 mmol), DMSO (1.0 mL), and acetone (615 µL, 8.36 mmol) was stirred at room temperature (25° C.) for 5 min. To this mixture, N-acetyl-D-mannosamine monohydrate (100.0 mg, 0.418 mmol) was added and the resulting mixture was stirred at the same temperature for 24 h. The mixture was purified by silica gel flash column chromatography (CH$_2$Cl$_2$/MeOH=92:8 to 83:17 over 10 min and 83:17 for 25 min) to give 2b (62.6 mg, 53%).

Example 5: Transformation of 2a to 2b Under the Pyrrolidine-Boric Acid Conditions To a solution of 2a (30.0 mg, 0.115 mmol) in DMSO (100 µL) was added H$_3$BO$_3$ (7.0 mg, 0.115 mmol) followed by pyrrolidine (5.0 µl, 0.57 mmol) at room temperature (25° C.), and the resulting mixture was stirred at the same temperature. Initially, the mixture was a clear colorless solution. After 1 h, the reaction mixture turned to pale yellow and the TLC analysis showed that 2a was consumed and 2b was formed. The mixture was purified silica gel flash column chromatography (CH$_2$Cl$_2$/MeOH=92:8 to 83:17 over 10 min and 83:17 for 25 min) to give 2b (18.0 mg, 60%). When compound 2a was treated with pyrrolidine alone or H$_3$BO$_3$ alone in DMSO at room temperature (25° C.) under the same conditions, no changes of 2a was detected after 1 h.

Compound 2a: N-((2R,3S,4R,5 S)-5-((R)-1,2-dihydroxyethyl)-4-hydroxy-2-(2-oxopropyl)tetrahydrofuran-3-yl)acetamide

[Chem.11]

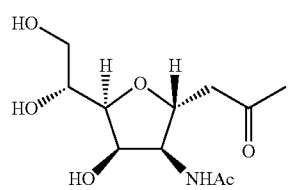

TABLE 1

R$_f$ = 0.32 (CH$_2$Cl$_2$/MeOH = 5:1).
Colorless crystals (crystallized from acetone); mp 157° C. [α]$_D^{25}$ + 59.3 (c 1.04, MeOH). $^1$H NMR (400 MHz, CD$_3$OD): δ 4.26 (dd, J = 4.0 Hz, 3.2 Hz, 1H), 4.23 (ddd, J = 9.6 Hz, 6.4 Hz, 5.2 Hz, 1H), 4.17 (dd, J = 9.6 Hz, 4.0 Hz, 1H), 3.94 (dd, J = 8.4 Hz, 3.2 Hz, 1H), 3.88 (ddd, J = 8.4 Hz, 6.0 Hz, 3.2 Hz, 1H), 3.73 (dd, J = 11.6 Hz, 3.2 Hz, 1H), 3.56 (dd, J = 11.6 Hz, 6.0 Hz, 1H), 2.704 (dd, J = 6.4 Hz, 1H), 2.702 (d, J = 5.2 Hz, 1H), 2.17 (s, 3H), 1.99 (s, 3H). $^{13}$C NMR (100 MHz, CD$_3$OD): δ 209.8, 173.6, 82.1, 77.3, 72.2, 71.4, 64.9, 59.0, 48.4, 30.6, 22.6. HRMS (ESI): calcd for C$_{11}$H$_{20}$NO$_6$ ([M + H]$^+$) 262.1285, found 262.1273.

Compound 2b: N-((2S,3S,4R,5S,6R)-4,5-dihydroxy-6-(hydroxymethyl)-2-(2-oxopropyl)tetrahydro-2H-pyran-3-yl)acetamide

[Chem.12]

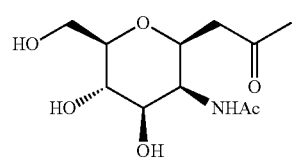

TABLE 2

R$_f$ = 0.27 (CH$_2$Cl$_2$/MeOH = 5:1).
Colorless gum. [α]$_D^{25}$ −29.0 (c 1.00, MeOH). Lit. [α]$_D$ −28.5 (c 0.45, H$_2$O).$^{52}$ $^1$H NMR (400 MHz, CD$_3$OD): δ 4.30 (dd, J = 4.4 Hz, 1.2 Hz, 1H), 4.03 (ddd, J = 7.2 Hz, 5.2 Hz, 1.2 Hz, 1H), 3.78 (d, J = 3.6 Hz, 2H), 3.69 (dd, J = 9.6 Hz, 4.4 Hz, 1H), 3.50 (t, J = 9.6 Hz, 1H), 3.22 (dt, J = 9.6 Hz, 3.6 Hz, 1H), 2.65 (dd, J = 17.2 Hz, 7.2 Hz, 1H), 2.54 (dd, J = 17.2 Hz, 5.2 Hz, 1H), 2.14 (s, 3H), 2.05 (s, 3H). $^{13}$C NMR (400 MHz, CD$_3$OD): δ 208.6, 174.5, 82.3, 75.1, 74.8, 68.3, 62.2, 54.1, 45.9, 30.4, 22.6. HRMS (ESI): calcd for C$_{11}$H$_{20}$NO$_6$ ([M + H]$^+$) 262.1285, found 262.1275.

Example 6: Reaction Using D-Proline and N,N-Diisopropylethylamine as Catalyst

A mixture of D-proline (78.0 mg, 0.68 mmol), DMSO (3.0 mL), acetone (1.99 mL, 27.1 mmol), and N,N-diisopropylethylamine (118 µL, 0.68 mmol) was stirred at room temperature (25° C.) for 5 min. To this mixture, N-acetyl-D-glucosamine (300 mg, 1.36 mmol) was added and the resulting mixture was stirred at the same temperature for 96 h. The mixture was purified by silica gel flash column chromatography (CH$_2$Cl$_2$/MeOH=90:10 to 83:17 over 10 min and 83:17 for 25 min) to give a mixture of 6a and 6b (7.7 mg, 2%).

Example 7: Reaction Using Pyrrolidine and Boric Acid (1 Equiv) as Catalyst

A mixture of pyrrolidine (111 µL, 1.36 mmol), H$_3$BO$_3$ (168.0 mg, 2.71 mmol), DMSO (6.0 mL), acetone (3.99 mL, 54.3 mmol), and N-acetyl-D-glucosamine (600 mg, 2.71 mmol) was stirred at room temperature (25° C.) for 24 h. The mixture was purified by silica gel flash column chromatography (CH$_2$Cl$_2$/MeOH=86:14 to 78:22 over 10 min and 78:22 for 25 min) to give 6a (156.0 mg, 22%, 6a-1/6a-2=1:3).

Example 8: Reaction Using Pyrrolidine and Boric Acid (2 Equiv) as Catalyst

A mixture of pyrrolidine (19.0 µL, 0.23 mmol), H$_3$BO$_3$ (56.0 mg, 0.90 mmol), DMSO (1.0 mL), acetone (0.66 mL, 9.0 mmol), and N-acetyl-D-glucosamine (100 mg, 0.45 mmol) was stirred at room temperature (25° C.) for 24 h. The mixture was purified by silica gel flash column chromatography (CH$_2$Cl$_2$/MeOH=86:14 to 78:22 over 10 min and 78:22 for 25 min) to give 6b (79.0 mg, 66%).

13

Compound 6a-1: N-((2R,3R,4R,5S)-5-((R)-1,2-dihydroxyethyl)-4-hydroxy-2-(2-oxopropyl)tetrahydrofuran-3-yl)acetamide

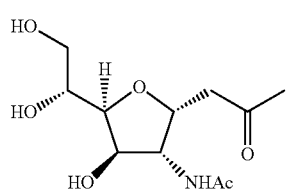

[Chem.13]

TABLE 3

$R_f$ = 0.30 (CH$_2$Cl$_2$/MeOH = 5:1).
Colorless oil (6a-1:6a-2 = 3:1). $^1$H NMR (400 MHz, CD$_3$OD) (6a-1 extracted from 6a-1:6a-2 = 3:1): δ 4.15 (dd, J = 4.0 Hz, 2.0 Hz, 1H), 4.04 (dt, J = 8.0 Hz, 2.0 Hz, 1H), 3.92-3.87 (m, 2H), 3.76 (dd, J = 8.4 Hz, 4.0 Hz, 1H), 3.74 (dd, J = 3.2 Hz, 1.2 Hz, 1H), 3.58 (dd, J = 11.2 Hz, 5.6 Hz, 1H), 2.94 (dd, J = 16.8 Hz, 8.0 Hz, 1H), 2.84 (dd, J = 11.2 Hz, 5.6 Hz, 1H), 2.94 (dd, J = 16.8 Hz, 8.0 Hz, 1H), 2.84 (dd, J = 16.8 Hz, 4.8 Hz, 1H), 2.16 (s, 3H), 1.96 (s, 3H). $^{13}$C NMR (100 MHz, CD$_3$OD): δ 209.6, 173.2, 82.2, 80.5, 77.7, 71.2, 65.1, 64.1, 49.1, 30.5, 22.5. HRMS (ESI) (6a-1:6a-2 = 3:1): calcd for C$_{11}$H$_{20}$NO$_6$ ([M + H]$^+$) 262.1285, found 262.1275.

Compound 6a-2: N-((2S,3R,4R,5S)-5-((R)-1,2-dihydroxyethyl)-4-hydroxy-2-(2-oxopropyl)tetrahydrofuran-3-yl)acetamide

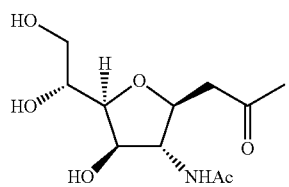

[Chem.14]

TABLE 4

$R_f$ = 0.24 (CH$_2$Cl$_2$/MeOH = 5:1).
Colorless oil (6a-1:6a-2 = 1:1). $^1$H NMR (400 MHz, CD$_3$OD) (6a-2 extracted from 6a-1:6a-2 = 1:1): δ 4.63 (ddd, J = 8.4 Hz, 5.6 Hz, 4.4 Hz, 1H), 4.32 (dd, J = 4.4 Hz, 1.2 Hz, 1H), 4.18 (dd, J = 3.6 Hz, 1.2 Hz, 1H), 3.94-3.89 (m, 2H), 3.75 (dd, J = 11.2 Hz, 3.0 Hz, 1H), 3.58 (dd, J = 11.2 Hz, 5.6 Hz, 1H), 2.73 (dd, J = 16.4 Hz, 8.4 Hz, 1H), 2.60 (dd, J = 16.4 Hz, 5.6 Hz, 1H), 2.16 (s, 3H), 1.97 (s, 3H). $^{13}$C NMR (100 MHz, CD$_3$OD) (6a-2 extracted from 6a-1:6a-2 = 1:1): δ 209.1, 173.2, 81.0, 77.3, 76.2, 71.1, 65.4, 60.6, 44.4, 30.4, 22.4. HRMS (ESI) (6a-1:6a-2 = 1:1): calcd for C$_{11}$H$_{20}$NO$_6$ ([M + H]$^+$) 262.1285, found 262.1291.

14

Compound 6b: N-((2S,3R,4R,5S,6R)-4,5-dihydroxy-6-(hydroxymethyl)-2-(2-oxopropyl)tetrahydro-2H-pyran-3-yl)acetamide

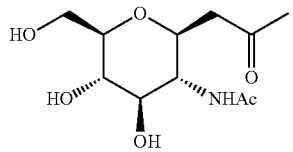

[Chem.15]

TABLE 5

$R_f$ = 0.22 (CH$_2$Cl$_2$/MeOH = 5:1).
Colorless crystals (crystallized from CH$_2$Cl$_2$—MeOH); mp 141° C.
$^1$H NMR (400 MHz, CD$_3$OD): δ 3.80 (dd, J = 12.0 Hz, 2.4 Hz, 1H), 3.75 (ddd, J = 9.6 Hz, 8.0 Hz, 4.0 Hz, 1H), 3.63 (dd, J = 12.0 Hz, 5.6 Hz, 1H), 3.62 (t, J = 9.6 Hz, 1H), 3.40 (dd, J = 9.6 Hz, 8.4 Hz, 1H), 3.32 (dd, J = 9.6 Hz, 8.4 Hz, 1H), 3.22 (ddd, J = 9.6 Hz, 5.6 Hz, 2.4 Hz, 1H), 2.67 (dd, J = 16.4 Hz, 8.0 Hz, 1H), 2.60, (dd, J = 16.4 Hz, 8.0 Hz, 1H), 2.16, (s, 3H), 1.96 (s, 3H). $^{13}$C NMR (100 MHz, D$_2$O): δ 209.6, 173.8, 81.7, 77.1, 76.3, 72.2, 62.8, 56.7, 47.3, 30.6, 22.8. HRMS (ESI): calcd for C$_{11}$H$_{19}$NO$_6$Na ([M + Na]$^+$) 284.1110, found 284.1105.

Example 9: Reaction Using D-Proline and N,N-Diisopropylethylamine as Catalyst

To a mixture of D-proline (22.0 mg, 0.19 mmol) in DMSO (1.0 mL), acetone (558 μL, 7.6 mmol) and N,N-diisopropylethylamine (33.0 μL, 0.19 mmol) were added at room temperature (25° C.), and the mixture was stirred for 5 min. To this mixture, N-valeryl-D-glucosamine (100.0 mg, 0.38 mmol) was added and the resulting mixture was stirred at the same temperature for 96 h. The mixture was purified by silica gel flash column chromatography (CH$_2$Cl$_2$/MeOH=90:10 to 83:17 over 10 min and 83:17 for 25 min) to give 8a (13.8 mg, 12%).

Example 10: Reaction Using Pyrrolidine and Boric Acid as Catalyst

A mixture of pyrrolidine (16.0 μL, 0.19 mmol), H$_3$BO$_3$ (23.0 mg, 0.38 mmol), DMSO (1.0 mL), and acetone (559 μL, 7.6 mmol) was stirred at room temperature (25° C.) for 5 min. To this mixture, N-valeryl-D-glucosamine (100.0 mg, 0.38 mmol) was added and the resulting mixture was stirred at the same temperature for 24 h. The mixture was purified by silica gel flash column chromatography (CH$_2$Cl$_2$/MeOH=90:10 to 83:17 over 10 min and 83:17 for 25 min) to give 8b (85.1 mg, 74%).

Compound 8a: N-((2S,3R,4R,5S)-5-((R)-1,2-dihydroxyethyl)-4-hydroxy-2-(2-oxopropyl)tetrahydrofuran-3-yl)pentanamide

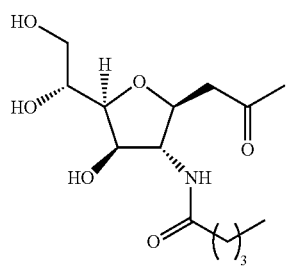

[Chem.16]

TABLE 6

$R_f$ = 0.49 (CH$_2$Cl$_2$/MeOH = 5:1).
Colorless gum. $^1$H NMR (400 MHz, CD$_3$OD): δ 4.64 (ddd, J = 8.0 Hz, 5.4 Hz, 4.4. Hz, 1H), 4.34 (dd, 4.4. Hz, 1.2 Hz, 1H), 4.16 (dd, J = 3.6 Hz, 1.2 Hz, 1H), 3.92 (dd, J = 8.4 Hz, 3.6 Hz, 1H), 3.88 (ddd, J = 8.4 Hz, 5.6 Hz, 3.2 Hz, 1H), 3.76 (dd, J = 11.2 Hz, 3.2 Hz, 1H), 3.58 (dd, J = 11.2 Hz, 5.6 Hz, 1H), 2.73 (dd, 1H, J = 16.4 Hz, 8.0 Hz, 1H), 2.59 (dd, J = 16.4 Hz, 5.4 Hz, 1H), 2.28-2.20 (m, 2H), 2.16 (s, 3H), 1.64-1.55 (m, 2H), 1.40-1.30 (m, 2H), 0.96-0.92 (m, 3H). $^{13}$C NMR (100 MHz, CD$_3$OD): δ 209.0, 176.3, 81.0, 77.4, 76.2, 71.2, 65.5, 60.5, 44.5, 36.5, 30.4, 29.3, 23.4, 14.1. HRMS (ESI): calcd for C$_{14}$H$_{26}$NO$_6$ ([M + H]$^+$) 304.1755, found 304.1760.

Compound 8b: N-((2S,3R,4R,5S,6R)-4,5-dihydroxy-6-(hydroxymethyl)-2-(2-oxopropyl)tetrahydro-2H-pyran-3-yl)pentanamide

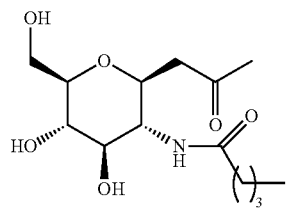

[Chem.17]

TABLE 7

$R_f$ = 0.42 (CH$_2$Cl$_2$/MeOH = 5:1).
Pale yellow solid. $^1$H NMR (400 MHz, CD$_3$OD): δ 3.80 (dd, J = 12.0 Hz, 2.4 Hz, 1H), 3.75 (ddd, J = 10.0 Hz, 8.4 Hz, 3.2 Hz, 1H), 3.63 (dd, J = 10.0 Hz, 9.6 Hz, 1H), 3.63 (dd, J = 12.0 Hz, 5.2 Hz, 1H), 3.40 (dd, J = 10.0 Hz, 8.4 Hz, 1H), 3.31 (dd, J = 10.0 Hz, 8.4 Hz, 1H), 3.22 (ddd, J = 9.6 Hz, 5.2 Hz, 2.4 Hz, 1H), 2.67 (dd, J = 16.4 Hz, 8.4 Hz, 1H), 2.57 (dd, J = 16.4 Hz, 3.2 Hz, 1H), 2.21 (dt, J = 2.4 Hz, 7.6 Hz, 2H), 2.16 (s, 3H), 1.63-1.55 (m, 2H), 1.40-1.31 (m, 2H), 0.93 (t, J = 7.6 Hz, 3H). $^{13}$C NMR (100 MHz, CD$_3$OD): δ 209.5, 176.8, 81.7, 77.1, 76.3, 72.3, 62.9, 56.5, 47.3, 37.1, 30.7, 29.0, 23.4, 14.1. HRMS (ESI): calcd for C$_{14}$H$_{26}$NO$_6$ ([M + H]$^+$) 304.1755, found 304.1756.

Example 11: Reaction Using D-Proline and N,N-Diisopropylethylamine as Catalyst in MeOH A mixture of D-proline (26.0 mg, 0.23 mmol), MeOH (1.0 mL), acetone (660 μL, 9.0 mmol), N,N-diisopropylethylamine (39.0 μL, 0.23 mmol), and N-acetyl-D-galactosamine (100 mg, 0.45 mmol) was stirred at room temperature (25° C.) for 24 h. The mixture was purified by silica gel flash column chromatography (CH$_2$Cl$_2$/MeOH=91:9 to 84:16 over 10 min and 84:16 for 25 min) to give 10a (103 mg, 88%, 10a-1:10a-2=1:1).

Example 12: Reaction Using D-Proline and N,N-Diisopropylethylamine as Catalyst in DMSO A mixture of D-proline (16.0 mg, 0.14 mmol), DMSO (1.0 mL), acetone (398 μL, 5.4 mmol), diisopropylethylamine (24.0 μL, 0.14 mmol), and N-acetyl-D-galactosamine (60.0 mg, 0.27 mmol) was stirred at room temperature (25° C.) for 24 h. The mixture was purified by silica gel flash column chromatography (CH$_2$Cl$_2$/MeOH=91:9 to 84:16 over 10 min and 84:16 for 25 min) to give 10a (19.0 mg, 26%, 10a-1:10a-2=1.4:1).

Example 13: Reaction Using D-Proline and N,N-Diisopropylethylamine as Catalyst in DMSO A mixture of D-proline (16.0 mg, 0.14 mmol), DMSO (1.0 mL), acetone (398 μL, 5.4 mmol), diisopropylethylamine (24.0 μL, 0.14 mmol), and N-acetyl-D-galactosamine (60.0 mg, 0.27 mmol) was stirred at room temperature (25° C.) for 24 h. The mixture was purified by silica gel flash column chromatography (CH$_2$Cl$_2$/MeOH=91:9 to 84:16 over 10 min and 84:16 for 25 min) to give 10a (19.0 mg, 26%, 10a-1:10a-2=1.4:1).

Example 14: Reaction Using Pyrrolidine and Boric Acid as Catalyst at 25° C.

A mixture of pyrrolidine (19.0 μL, 0.23 mmol), H$_3$BO$_3$ (28.0 mg, 0.45 mmol), DMSO (1.0 mL), acetone (0.66 mL, 9.0 mmol), and N-acetyl-D-galactosamine (100 mg, 0.45 mmol) was stirred at room temperature (25° C.) for 24 h. The mixture was purified by silica gel flash column chromatography (CH$_2$Cl$_2$/MeOH=91:9 to 84:16 over 10 min and 84:16 for 25 min) to give 10a-1 (17.0 mg, 15%) and 10a-2 (17.0 mg, 15%), 10b (7.0 mg, 6%).

Compound 10a-1: N-((2R,3R,4R,5R)-5-((R)-1,2-dihydroxyethyl)-4-hydroxy-2-(2-oxopropyl)tetrahydrofuran-3-yl)acetamide

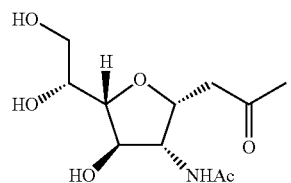

[Chem.18]

TABLE 8

$R_f$ = 0.29 (CH$_2$Cl$_2$/MeOH = 5:1).
Colorless gum. [α]$_D^{25}$ +7.1 (c 0.17, MeOH). $^1$H NMR (400 MHz, CD$_3$OD): δ 4.46 (ddd, J = 8.0 Hz, 5.2 Hz, 4.4 Hz, 1H), 4.21 (dd, J = 4.4 Hz, 2.0 Hz, 1H), 4.08 (dd, J = 3.6 Hz, 2.0 Hz, 1H), 3.75 (dd, J = 3.6 Hz, 2.4 Hz, 1H), 3.73 (ddd, J = 6.8 Hz, 5.6 Hz, 2.4 Hz, 1H), 3.60 (dd, J = 10.8 Hz, 5.6 Hz, 1H), 3.57 (dd, J = 10.8 Hz, 6.8 Hz, 1H), 2.71 (dd, J = 16.8 Hz, 8.0 Hz, 1H), 2.61 (dd, J = 16.8 Hz, 5.2 Hz, 1H), 2.16 (s,

TABLE 8-continued

3H), 1.97 (s, 3H). $^{13}$C NMR (100 MHz, CD$_3$OD): δ 209.0, 172.6, 86.4, 79.2, 77.1, 72.6, 64.4, 60.2, 44.2, 30.3, 22.7. HRMS (ESI): calcd for C$_{11}$H$_{20}$NO$_6$ ([M + H]$^+$) 262.1285, found 262.1275.

Compound 10a-2: N-((2S,3R,4R,5R)-5-((R)-1,2-dihydroxyethyl)-4-hydroxy-2-(2-oxopropyl)tetrahydrofuran-3-yl)acetamide

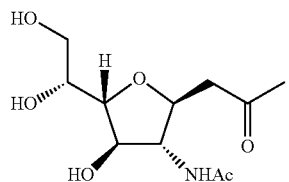

[Chem.19]

TABLE 9

$R_f$ = 0.25 (CH$_2$Cl$_2$/MeOH = 5:1).
Colorless gum. [α]$_D^{25}$ −10.5 (c 0.38, MeOH). $^1$H NMR (400 MHz, CD$_3$OD): δ 4.19 (t, J = 7.2 Hz, 1H), 4.14 (ddd, J = 7.2 Hz, 6.8 Hz, 4.4 Hz, 1H), 4.09 (dd, J = 7.2 Hz, 6.8 Hz, 1H), 3.83 (dd, J = 7.2 Hz, 2.8 Hz, 1H), 3.65 (ddd, J = 6.8 Hz, 5.6 Hz, 2.8 Hz, 1H), 3.58 (d, J = 5.6 Hz, 1H), 3.58 (d, J = 6.8 Hz, 1H), 2.84 (dd, J = 16.8 Hz, 7.2 Hz, 1H), 2.79 (d, J = 16.8 Hz, 4.4 Hz, 1H), 2.17 (s, 3H), 1.96 (s, 3H). $^{13}$C NMR (100 MHz, CD$_3$OD): δ 209.9, 173.8, 83.8, 78.8, 76.6, 72.6, 64.4, 62.4, 48.6, 30.6, 22.7. HRMS (ESI): calcd for C$_{11}$H$_{20}$NO$_6$ ([M + H]$^+$) 262.1285, found 262.1288.

Compound 10b: N-((2S,3R,4R,5R,6R)-4,5-dihydroxy-6-(hydroxymethyl)-2-(2-oxopropyl)tetrahydro-2H-pyran-3-yl)acetamide

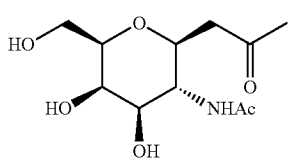

[Chem.20]

TABLE 10

$R_f$ = 0.21 (CH$_2$Cl$_2$/MeOH = 5:1).
Colorless solid. [α]$_D^{25}$ +19.4 (c 0.73, MeOH). $^1$H NMR (400 MHz, CD$_3$OD): δ 3.91 (t, J = 10.4 Hz, 1H), 3.87 (dd, J = 3.2 Hz, 0.8 Hz, 1H), 3.70 (ddd, J = 10.4 Hz, 8.8 Hz, 3.2 Hz, 1H), 3.663 (d, J = 6.8 Hz, 1H), 3.661 (d, J = 5.6 Hz, 1H), 3.53 (dd, J = 10.4 Hz, 3.2 Hz, 1H), 3.45 (ddd, J = 6.8 Hz, 5.6 Hz, 0.8 Hz, 1H), 2.72 (dd, J = 16.6 Hz, 8.8 Hz, 1H), 2.62 (dd, J = 16.6 Hz, 3.2 Hz, 1H), 2.16 (s, 3H), 1.96 (s, 3H). $^{13}$C NMR (100 MHz, CD$_3$OD): δ 209.7, 174.1, 80.2, 76.7, 74.0, 70.0, 62.6, 53.2, 47.3, 30.7, 22.9. HRMS (ESI): calcd for C$_{11}$H$_{20}$NO$_6$ ([M + H]$^+$) 262.1285, found 262.1289.

Example 15: Reaction of N-Acetyl-D-Glucosamine (5) with Methoxyacetone Using Pyrrolidine and Boric Acid as Catalyst A mixture of H$_3$BO$_3$ (28.0 mg, 0.45 mmol) and N-acetyl-D-glucosamine (100 mg, 0.45 mmol) in DMSO (1.0 mL) was stirred at room temperature (25° C.) for 15 min. To the mixture, methoxyacetone (0.83 mL, 9.0 mmol) and pyrrolidine (19.0 μL, 0.23 mmol) were added and the resulting mixture was stirred at the same temperature for 36 h. The mixture was purified by silica gel flash column chromatography (CH$_2$Cl$_2$/MeOH=86:14 to 79:21 over 10 min and 79:21 for 25 min) to give 11 (86.0 mg, 66%, α-isomer:β-isomer=1:1).

Compound 11: N-((3R,4R,5S,6R)-4,5-dihydroxy-6-(hydroxymethyl)-2-(3-methoxy-2-oxopropyl)tetrahydro-2H-pyran-3-yl)acetamide

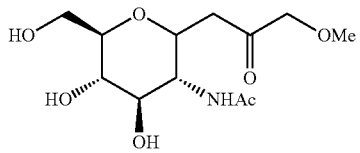

[Chem.21]

TABLE 11

$R_f$ = 0.32 (a 1:1 mixture of α- and β-isomers, CH$_2$Cl$_2$/MeOH = 5:1).
Colorless gum. $^1$H NMR (400 MHz, CD$_3$OD) (α-isomer:β-isomer = 1:1): δ 4.68-4.62 (m, 1H × ½), 4.34-4.31 (m, 1H × ½), 4.19-4.03 (m, 2H + 1H + 1H × ½), 3.95-3.71 (m, 3H + 1H × ½), 3.61-3.55 (m, 1H), 3.38 (s, 3H), 2.92 (dd, J = 16.2 Hz, 8.4 Hz, 1H × ½), 2.77 (dd, J = 16.2 Hz, 4.4 Hz, 1H × ½), 2.72 (dd, J = 16.2 Hz, 8.4 Hz, 1H × ½), 2.77 (dd, J = 16.2 Hz, 5.4 Hz, 1H × ½), 1.98 (s, 3H × ½), 1.96 (s, 3H × ½). $^{13}$C NMR (100 MHz, CD$_3$OD) (α-isomer:β-isomer = 1:1): δ 208.5, 208.2, 173.2, 82.2, 81.0, 80.3, 78.7, 78.5, 77.6, 77.2, 76.1, 71.2, 71.1, 65.4, 65.1, 64.1, 60.6, 59.5, 44.7, 40.0, 22.5, 22.4. HRMS (ESI): calcd for C$_{12}$H$_{22}$NO$_7$ ([M + H]$^+$) 292.1391, found 262.1394.

Example 16: Allylation Reaction of 2a with Allyl Bromide and Indium

To a solution of 2a (50.0 mg, 0.191 mmol) in DMF (4.0 mL) and water (0.5 mL) were added allyl bromide (165 μL, 1.91 mmol) and In (22.0 mg, 0.191 mmol) at room temperature (25° C.). The resulting mixture was stirred at the same temperature for 18 h. The mixture was purified by silica gel flash column chromatography (CH$_2$Cl$_2$/MeOH=95:5 to 88:12 over 10 min and 88:12 for 25 min) to give 12 (100.3 mg, 88%).

Compound 12: N-((2R,3S,4R,5 S)-5-((R)-1,2-dihydroxyethyl)-4-hydroxy-2-(2-hydroxy-2-methylpent-4-en-1-yl)tetrahydrofuran-3-yl)acetamide

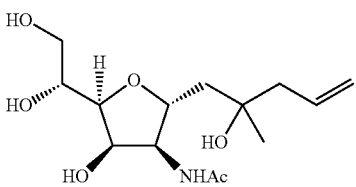

[Chem. 22]

TABLE 12

Colorless gum. $^1$H NMR (400 MHz, CD$_3$OD): δ 5.95-5.81(m, 1H), 5.09-5.02 (m, 2H), 4.27-4.21 (m, 1H), 4.12-4.05 (m, 2H), 3.95-3.85 (m, 2H), 3.78-3.73 (m, 1H), 3.59 (dd, J = 11.4 Hz, 5.4 Hz, 1H), 2.35-2.19 (m, 2H), 2.00 (s, 3H), 1.74-1.61 (m, 2H), 1.19 (s, 3H). $^{13}$C NMR (100 MHz, CD$_3$OD): δ 173.5, 135.9, 135.7, 118.1, 118.0, 82.1, 82.0, 77.8, 77.6, 72.9, 72.8, 71.6, 71.44, 71.40, 65.10, 65.07, 60.0, 47.6, 45.9, 45.7, 27.5, 27.0, 22.6. HRMS (ESI): calcd for C$_{14}$H$_{26}$NO$_6$ ([M + H]$^+$) 304.1755, found 304.1760.

Example 17: Reaction of N-Acetyl-D-Mannosamine (1) with Methoxyacetone

A mixture of L-proline (24.0 mg, 0.21 mmol), DMSO (1.0 mL), methoxyacetone (78 μL, 8.4 mmol), N,N-diisopropylethylamine (36.0 μL, 0.21 mmol), and N-acetyl-D-mannosamine monohydrate (100.0 mg, 0.42 mmol) was stirred at room temperature (25° C.) for 24 h. The mixture was purified by silica gel flash column chromatography (CH$_2$Cl$_2$/MeOH=90:10 to 83:17 over 10 min and 83:17 for 25 min) to give compound 13 (11.0 mg, 8.8%).

Compound 13: N-((2R,3S,4R,5S)-5-((R)-1,2-dihydroxyethyl)-4-hydroxy-2-(3-methoxy-2-oxopropyl)tetrahydrofuran-3-yl)acetamide

[Chem.23]

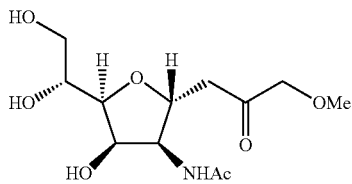

TABLE 13

R$_f$ = 0.38 (CH$_2$Cl$_2$/MeOH = 5:1).
Colorless gum. $^1$H NMR (400 MHz, CD$_3$OD): δ 4.32-4.18 (m, 3H), 4.14 (s, 2H), 3.94 (dd, J = 8.0 Hz, 3.2 Hz, 1H), 3.87 (ddd, J = 8.0 Hz, 5.6 Hz, 3.2 Hz, 1H), 3.72 (dd, J = 11.2 Hz, 3.2 Hz, 1H), 3.56 (dd, J = 11.2 Hz, 5.6 Hz, 1H), 3.38 (s, 3H), 2.70 (dd, J = 16.0 Hz, 7.2 Hz, 1H), 2.63 (dd, J = 16.0 Hz, 3.2 Hz, 1H), 1.99 (s, 3H). $^{13}$C NMR (100 MHz, CD$_3$OD): δ 208.6, 173.6, 82.2, 78.8, 77.3, 72.2, 71.4, 64.9, 59.4, 59.1, 43.9, 22.6. HRMS (ESI): calcd for C$_{12}$H$_{22}$NO$_7$ ([M + H]$^+$) 292.1391, found 262.1397.

Example 18: Reaction of 2a with Sulfonyl Hydrazide

To a solution of 2a (50.0 mg, 0.19 mmol) in DMSO (1.0 mL) was added p-toluenesulfonyl hydrazide (46.0 mg, 0.25 mmol) at room temperature (25° C.) and the mixture was stirred at 40° C. for 16 h. The mixture was purified by silica gel flash column chromatography (CH$_2$Cl$_2$/MeOH=93:7 to 85:15 over 10 min and 85:15 for 25 min) to give 14a (15.4 mg, 19%) and 14b (41.5 mg, 50%).

Compound 14 (14a and 14b): N-((2R,3 S,4R,5 S)-5-((R)-1,2-dihydroxyethyl)-4-hydroxy-2-(2-(2-tosylhydrazono)propyl) tetrahydrofuran-3-yl)acetamide

[Chem.24]

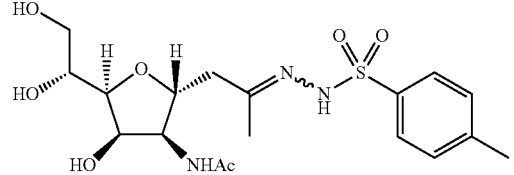

TABLE 14

R$_f$ = 0.44 (CH$_2$Cl$_2$/MeOH 8:1).
Colorless gum. $^1$H NMR (400 MHz, CD$_3$OD): δ 7.80 (d, J = 8.2 Hz, 2H), 7.37 (d, J = 8.2 Hz, 2H), 4.24 (t, J = 3.2 Hz, 1H), 4.09 (dd, J = 9.6 Hz, 3.2 Hz, 1H), 4.05 (ddd, J = 9.6 Hz, 7.6 Hz, 2.8 Hz, 1H), 3.92 (dd, J = 8.4 Hz, 3.2 Hz, 1H), 3.83 (ddd, J = 8.4 Hz, 6.2 Hz, 3.0 Hz, 1H), 3.70 (dd, J = 11.4 Hz, 3.0 Hz, 1H), 3.53 (dd, J = 11.4 Hz, 6.2 Hz, 1H), 2.55 (dd, J = 14.8 Hz, 7.6 Hz, 1H), 2.49 (dd, J = 14.8 Hz, 2.8 Hz, 1H), 2.43 (s, 3H),
2.01 (s, 3H), 1.92 (s, 3H). $^{13}$C NMR (100 MHz, CD$_3$OD): δ 173.7, 158.9, 145.2, 137.3, 130.5, 129.1, 82.3, 78.9, 71.8, 71.4, 65.0, 59.0, 36.1, 24.0, 22.6, 21.5. HRMS (ESI): calcd for C$_{18}$H$_{28}$N$_3$O$_7$S ([M + H]$^+$) 430.1642, found 430.1596.

TABLE 15

R$_f$ = 0.31 (CH$_2$Cl$_2$/MeOH 8:1).
Colorless gum. $^1$H NMR (400 MHz, CD$_3$OD): δ 7.80 (d, J = 8.4 Hz, 2H), 7.37 (d, J = 8.4 Hz, 2H), 4.25 (m, 1H), 4.10-4.02 (m, 2H), 3.84-3.77 (m, 2H), 3.68-3.62 (m, 1H), 3.50-3.45 (m, 1H), 2.49-2.34 (m, 2H), 2.42 (s, 3H), 2.42 (s,), 1.99 (s, 3H), 1.85 (s, 3H). $^{13}$C NMR (100 MHz, CD$_3$OD): δ 173.7, 159.0, 145.2, 137.4, 130.5, 129.0, 81.8, 78.7, 72.0, 71.4, 65.0, 59.5, 43.3, 22.7, 21.5, 17.3. HRMS (ESI): calcd for C$_{18}$H$_{28}$N$_3$O$_7$S ([M + H]$^+$) 430.1642, found 430.1599.

INDUSTRIAL APPLICABILITY

The present invention can provide novel C-glycoside derivatives which are biologically important under high stereoselective, mild, atom economical condition.

The invention claimed is:
1. A process for the manufacture of a compound of formula I or a compound of formula II:

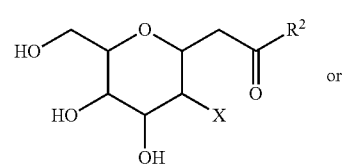

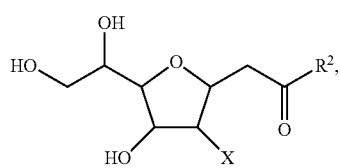

wherein
X is OH or NHCOR$^1$,
R$^1$ is C$_{1-7}$alkyl, C$_{3-7}$cycloalkyl, halo-C$_{1-7}$alkyl, or C$_{1-7}$alkoxy-C$_{1-7}$alkyl, and
R$^2$ is C$_{1-7}$alkyl, C$_{3-7}$ cycloalkyl, halo-C$_{1-7}$alkyl, C$_{1-7}$alkoxy, halo-C$_{1-7}$alkoxy, or C$_{1-7}$alkoxy-C$_{1-7}$alkyl,
said method comprising step A):
reacting a compound of formula III:

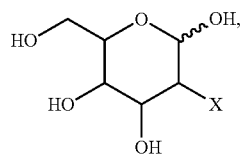

III wherein X is as defined above,
with a compound of formula IV:

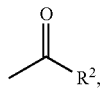

IV wherein R$^2$ is as defined above,
in the presence of a 5- or 6-membered heterocyclic secondary amine, and an additive selected from the group consisting of a tertiary amine, a boronic compound, and a hydroxycarboxylic acid derivative.

2. The process according to claim 1, wherein the 5- or 6-membered heterocyclic secondary amine and the additive are selected from the group consisting of
(a) pyrrolidine and H$_3$BO$_3$,
(b) L-proline and iPr$_2$NEt,
(c) L-proline, iPr$_2$NEt, and cis-4-hydroxy-cyclohexane carboxylic acid, and
(d) D-proline and iPr$_2$NEt.

3. The process according to claim 1, wherein the 5- or 6-membered heterocyclic secondary amine is selected from the group consisting of pyrrolidine, L-proline, and D-proline.

4. The process according to claim 1, wherein
the tertiary amine is selected from the group consisting of trimethylamine, triethylamine, diisopropylethylamine, pyridine, and pyrimidine,
the boronic compound is selected from the group consisting of H$_3$BO$_3$, methyl boronic acid, phenyl boronic acid, dimethyl borinic acid, and diethyl borinic acid, and
the hydroxycarboxylic acid derivative is selected from the group consisting of a 5-membered hydroxycarboxylic acid derivative, a 6-membered hydroxycarboxylic acid derivative, and an amino acid derivative.

5. A process for the manufacture of a compound of formula I-1, II-1, I-2, or II-2:

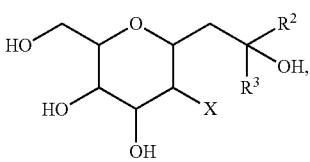

I-1

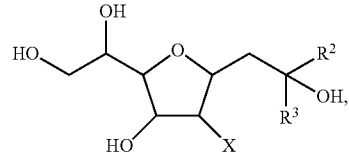

II-1

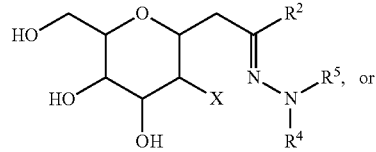

I-2

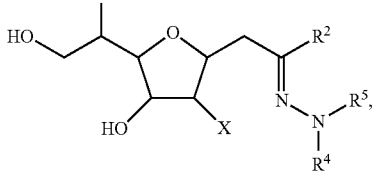

II-2 said method comprising step A):
reacting a compound of formula III:

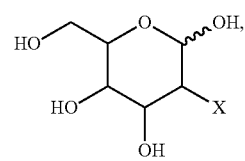

III wherein X is OH or NHCOR$^1$, and
R$^1$ is C$_{1-7}$alkyl, C$_{3-7}$ cycloalkyl, halo-C$_{1-7}$alkyl, or C$_{1-7}$alkoxy-C$_{1-7}$alkyl,
with a compound of formula IV:

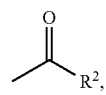

IV wherein R$^2$ is C$_{1-7}$alkyl, C$_{3-7}$cycloalkyl, halo-C$_{1-7}$alkyl, C$_{1-7}$ alkoxy, halo-C$_{1-7}$alkoxy, or C$_{1-7}$alokoxy-C$_{1-7}$alkyl,
in the presence of a 5 or 6-membered heterocyclic secondary amine, and an additive selected from the group consisting of a tertiary amine, a boronic compound, and a hydroxycarboxylic acid derivative,
to obtain a compound of formula I or II:

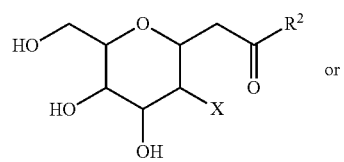

I

-continued

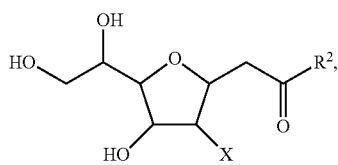

wherein X and R² are as defined above, and step B):

reacting the compound of formula I or II with a reactant to obtain a compound of formula I-1, II-1, I-2, or II-2:

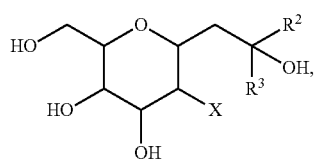

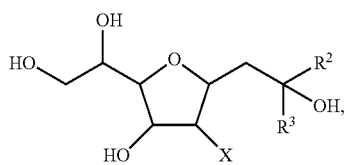

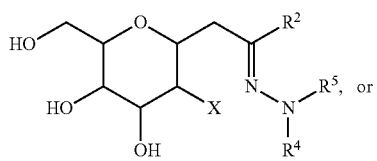

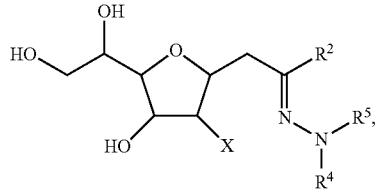

wherein

X, R¹, and R² are as defined above,

R³ is $C_{1-7}$alkyl, $C_{2-7}$alkenyl, or $C_{2-7}$alkynyl, and

R⁴ and R⁵ may be same or different, and each is independently selected from the group consisting of H, $C_{1-7}$alkyl, phenyl, benzyl, piperidinyl, p-tosyl and 1-phtalazinyl.

6. The process according to claim 5, wherein the reactant is allyl bromide and indium, or p-toluenesulfonyl hydrazide.

7. The process according to claim 5, wherein the 5- or 6-membered heterocyclic secondary amine and the additive are selected from the group consisting of
(a) pyrrolidine and $H_3BO_3$,
(b) L-proline and $iPr_2NEt$,
(c) L-proline, $iPr_2NEt$, and cis-4-hydroxy-cyclohexane carboxylic acid, and
(d) D-proline and $iPr_2NEt$.

8. The process according to claim 5, wherein the 5- or 6-membered heterocyclic secondary amine is selected from the group consisting of pyrrolidine, Lproline, and D-proline.

9. The process according to claim 5, wherein
the tertiary amine is selected from the group consisting of trimethylamine, triethylamine, diisopropylethylamine, pyridine, and pyrimidine,
the boronic compound is selected from the group consisting of $H_3BO_3$, methyl boronic acid, phenyl boronic acid, dimethyl borinic acid, and diethyl borinic acid, and
the hydroxycarboxylic acid derivative is selected from the group consisting of a 5-membered hydroxycarboxylic acid derivative, a 6-membered hydroxycarboxylic acid derivative, and an amino acid derivative.

* * * * *